US012680018B2

(12) United States Patent
Favereau et al.

(10) Patent No.: US 12,680,018 B2
(45) Date of Patent: Jul. 14, 2026

(54) CIRCULARLY POLARIZED OLED EMITTING LAYER COMPOSITION

(71) Applicants: UNIVERSITE DE RENNES, Rennes (FR); CENTRE NATIONAL DE LA RECHERCHE SCIENTIFIQUE—CNRS, Paris (FR); INSTITUT NATIONAL DES SCIENCES APPLIQUEES DE RENNES, Rennes Cédex (FR); ECOLE NATIONALE SUPERIEURE DE CHIMIE DE RENNES, Rennes (FR); COMMISSARIAT A L'ENERGIE ATOMIQUE ET AUX ENERGIES ALTERNATIVES, Paris (FR)

(72) Inventors: Ludovic Favereau, Montauban de Bretagne (FR); Jeanne Crassous, Thorigné-Fouillard (FR); Sitthichok Kasemthaveechok, Rennes (FR); Kais Dhbaibi, L'Hermitage (FR); Grégory Pieters, Grenoble Cedex (FR); Benoit Racine, Grenoble Cedex (FR); Etienne Quesnel, Grenoble Cedex (FR)

(73) Assignees: UNIVERSITE DE RENNES, Rennes (FR); CENTRE NATIONAL DE LA RECHERCHE SCIENTIFIQUE - CNRS -, Paris (FR); INSTITUT NATIONAL DES SCIENCES APPLIQUEES DE RENNES, Rennes (FR); COMMISSARIAT A L'ENERGIE ATOMIQUE, Paris (FR); ECOLE NATIONALE SUPERIEURE DE CHIMIE DE RENNES ET AUX ENERGIES ALTERNATIVES, Rennes (FR)

( * ) Notice: Subject to any disclaimer, the term of this patent is extended or adjusted under 35 U.S.C. 154(b) by 0 days.

(21) Appl. No.: 18/250,762

(22) PCT Filed: Oct. 29, 2021

(86) PCT No.: PCT/EP2021/080208
§ 371 (c)(1),
(2) Date: Apr. 27, 2023

(87) PCT Pub. No.: WO2022/090514
PCT Pub. Date: May 5, 2022

(65) Prior Publication Data

US 2023/0397490 A1 Dec. 7, 2023

(30) Foreign Application Priority Data

Oct. 30, 2020 (FR) ........................................ 2011121

(51) Int. Cl.
*C09K 11/06* (2006.01)
*C07C 211/50* (2006.01)
(Continued)

(52) U.S. Cl.
CPC ............ *C09K 11/06* (2013.01); *C07C 211/50* (2013.01); *C07C 255/51* (2013.01);
(Continued)

(58) Field of Classification Search
CPC .................................................... H10K 85/624
See application file for complete search history.

(56) References Cited

U.S. PATENT DOCUMENTS

| | | | | |
|---|---|---|---|---|
| 2016/0104855 | A1 | 4/2016 | Ohsawa et al. | |
| 2020/0083460 | A1 | 3/2020 | Duan et al. | |
| 2021/0119143 | A1* | 4/2021 | Tang | H10K 85/626 |

FOREIGN PATENT DOCUMENTS

| | | | |
|---|---|---|---|
| EP | 3644386 | A1 | 4/2020 |
| JP | 2017054870 | A | 3/2017 |

OTHER PUBLICATIONS

Schaack et al., "Helicene Monomers and Dimers: Chiral Chromophores Featuring Strong Circularly Polarized Luminescence", Chemistry a European Journal, Wiley-VCH Verlag GmbH & Co. KgaA, 2019, vol. 25, pp. 8003-8007.

(Continued)

*Primary Examiner* — William D Young
(74) *Attorney, Agent, or Firm* — Maier & Maier, PLLC

(57) ABSTRACT

An active light-emitting layer composition including a thermally activated delayed fluorescence (TADF) molecule with
(Continued)

TADF properties as a host material and a luminescent molecule with circularly polarized (CP) properties as a dopant. Also, a light-emitting device, such as an organic light-emitting diodes (OLED), including the active light-emitting layer made of this composition.

13 Claims, 3 Drawing Sheets

(51) Int. Cl.

| | |
|---|---|
| ***C07C 255/51*** | (2006.01) |
| ***C07D 213/06*** | (2006.01) |
| ***C09K 11/02*** | (2006.01) |
| ***H10K 50/80*** | (2023.01) |
| ***H10K 85/60*** | (2023.01) |
| ***H10K 101/20*** | (2023.01) |

(52) U.S. Cl.

CPC ............ *C07D 213/06* (2013.01); *C09K 11/02* (2013.01); *H10K 50/868* (2023.02); *H10K 85/624* (2023.02); *H10K 85/654* (2023.02); *C07C 2603/54* (2017.05); *C09K 2211/1007* (2013.01); *C09K 2211/1011* (2013.01); *C09K 2211/1018* (2013.01); *H10K 2101/20* (2023.02)

(56) References Cited

OTHER PUBLICATIONS

Dhbaibi et al., "Modulation of Circularly Polarized Luminescence Through Excited-State Symmetry Breaking and Interbranched Exciton Coupling in Helical Push-Pull Organic Systems", Chemical Science, The Royal Society of Chemistry, 2020, vol. 11, pp. 567-576.

Dhbaibi et al., "Exciton Coupling in Diketopyrrolopyrrole-Helicene Derivatives Leads to Red and Near-Infrared Circularly Polarized Luminescence", Chemical Science, The Royal Society of Chemistry, 2018, vol. 9, pp. 735-742.

International Search Report issued on Jan. 19, 2022, in corresponding International Patent Application No. PCT/EP2021/080208; 3 pages.

Bo Zhao et al: "Highly efficient red OLEDs using DCJTB as the dopant and delayed fluorescent exciplex as the host", Scientific Reports, vol. 5, No. 1, May 29, 2015 (May 29, 2015), pp. 1-8, 8 pgs.

Zhou Ling et al: "Emerging circularly polarized thermally activated delayed fluorescence materials and devices", Applied Physics Letters, AIP Publishing LLC, US, vol. 117, No. 13, Sep. 30, 2020 (Sep. 30, 2020), 5 pgs.

Byeon Sung Yong et al: "Recent Progress of Singlet-Exciton-Harvesting Fluorescent Organic Light-Emitting Diodes by Energy Transfer Processes", Advanced Materials, vol. 31, No. 34, Feb. 13, 2019 (Feb. 13, 2019), p. 1803714, 15 pgs.

Dongdong Zhang et al: "High-Efficiency Fluorescent Organic Light-Emitting Devices Using Sensitizing Hosts with a Small Singlet-Triplet Exchange Energy", Advanced Materials, vol. 26, No. 29, Aug. 1, 2014 (Aug. 1, 2014), pp. 5050-5055.

Han Jianmei et al: "Concentration-dependent circularly polarized luminescence of chiral cyclometalated platinum(II) complexes for electroluminescence", Journal of Organometallic Chemistry, Elsevier, Amsterdam, NL, vol. 915, Mar. 19, 2020 (Mar. 19, 2020), 8 pgs.

* cited by examiner

CIRCULARLY POLARIZED OLED EMITTING LAYER COMPOSITION

FIELD

This disclosure relates to the technical field of compositions for organic light-emitting diodes (OLEDs) which are capable of emitting circularly polarized light and also to light emitting devices incorporating such compositions. More in particular, this disclosure relates to the technical field of compositions for OLED light emitting layer or active layer.

BACKGROUND

Flat panel displays are ubiquitous in modern life. They are widely used in small and large devices alike such as mobile phones, TV sets, tablet computers, e-readers, VR (Virtual Reality) headsets, wearable smart devices and other electronic products. Such flat panel displays have been predominantly provided by LCDs, e.g. Twisted Nematic LCDs (TN-LCDs) and Super-Twisted Nematic LCDs (STN-LCDs). However, such devices have low intrinsic brightness and intense backlighting is required leading to higher power consumption.

The development of organic light-emitting diodes (OLED) offers the prospect of brighter and yet more power-saving devices. Indeed, OLEDs have the advantages of low operating voltages and low power consumption, fast response, wide viewing angle, high brightness and contrast ratios. Thus, they are seen as the most promising next-generation display technology.

An OLED panel typically comprises a first electrode, a second electrode and a functional structure layer between then first and second electrodes. The functional structure layer comprises a hole injection layer, a first hole transport layer, a second hole transport layer, an organic light-emitting layer, an electron transport layer and an electron injection layer sequentially laminated on the first electrode. The OLED technology can be divided into two main families of OLED depending on the nature of the luminescent material composing the organic-light-emitting layer: those based on small molecules and those employing polymers.

Research on OLED materials and devices has made significant progress. Recently, researchers have been investigating the manufacturing of circularly polarized OLED (CP-OLED). In comparison with unpolarized OLED, CP-OLED provides better contrast which makes it possible to decrease the overall brightness needed to obtain the same contrast level as in unpolarized OLED. Decreasing the overall brightness results in turn in lower power consumption.

To this day, the most efficient strategy is to use molecules that are capable of auto-assembling at the supramolecular scale to obtain an amplification of light polarization at the output. To this aim, a chiral liquid crystal passive filter can be used before a light source generated by another molecule. This makes it possible to have a polarization rate of about few tens percent. Another possibility is to use crystal liquid type luminescent polymers either through an intrinsically chiral polymer or an achiral polymer doped with a chiral molecule. This makes it possible to reach high polarization rates.

For example, EP 1523533 B1 describes a composition comprising a chiral, helical liquid crystalline phase with a substantially fixed, temperature independent helical pitch composed of calamitic (rod-like) liquid crystal molecules having a luminescent moiety. The composition is in mesophase, i.e. a phase between a liquid and a crystalized solid phase.

Another example is EP 2877552 B2, which describes a composition made of an electroluminescent polymer—such as poly(arylene vinylene) derivatives—and a scalemic chiral non-luminescent dopant—such as a helicene—which are blended together.

The principle of both documents relies on the use of pure fluorescence emitters. While the solutions provided by these two documents may show very high levels of circular polarization property, the maximum of internal quantum yield that these systems can reach is theoretically limited to 25%. Thus, the CP-OLEDs made through these approaches suffer from limited efficacy performances hindering their use in larger scale applications.

The second approach lies in the use of chiral emitting entities within an electrically conducting matrix to directly generate circularly polarized light. This strategy is easier to implement and its performances entirely depend on the intrinsic performance of the emitting entity. It has been proven difficult to find a molecule combining both a high luminescence property and high polarization rate. For example, lanthanide complexes have been used which have intense circular polarization rates of light, up to 75%, but present poor chemical stability and very limited luminescence efficacy.

Other purely organic molecules are currently being investigated. These organic molecules are interesting because they exhibit a high internal operation yield of about 100%. Such molecules have thermally activated delayed fluorescence (TADF) properties, hereafter TADF molecules. TADF is a process through in which upon electrical of optical excitation of the TADF molecule, its excited-state will be in equilibrium between the singlet and triplet spin configurations to some extent, which is governed by the energy gap between these two states ($\Delta E_{ST}$). During that period of time, the equilibrium is shifted toward the singlet state since its deactivation though fluorescence emission occurs much faster than phosphorescence emission from the triplet state (ns vs. μs, respectively). Finally, there are two fluorescence emission processes, one occurring directly from the singlet state (prompt fluorescence, ns timescale) and another one that is delayed in time (delayed fluorescence, μs timescale) due to the formation of the singlet-triplet excited states equilibrium. This equilibrium is very important for instance in OLEDs since it could lead to a theoretical internal quantum efficiency of 100%, in comparison to the maximum of 25% for pure fluorescence emitters mentioned above.

Thus, the current approach concerning such molecules is to combine within a single molecule both TADF and CP properties, which would ease the manufacturing process of CP-OLEDs. Designing such chiral TADF molecular emitters for CP-OLEDs is a highly challenging task because such compounds should combine chemical and photophysical properties for reaching both TADF process and exhibiting intense chiroptical properties at the same time (and high racemization barrier for vacuum deposition). Even if recent examples have nicely shown that a synergy between TADF and chiroptical properties could be readily obtained, tuning either one of the chemical/photophysical and chiroptical properties without disturbing the other seems a challenging task and only compromises can be reached.

However, to this day, the performances of such molecules have proven to be insufficient in terms of luminescence polarization rate. Indeed, up to now, the best molecule with both TADF and CP properties has reached an intensity of polarization, glum, of around $5\times10^{-3}$ (Chen et al., Chem. Commun., 2020, 56, 9380-9383).

SUMMARY

Therefore, there is still a need for improved light-emitting layer composition in the OLED technical field.

To this aim, the present invention provides an active light-emitting layer composition comprising a TADF molecule with TADF properties as a host material and a luminescent molecule with CP properties as a dopant.

Thus the approach of the invention is a bimolecular strategy within the active light-emitting layer which combines a first TADF molecule with a high conversion rate of the electrical excitation into light energy and capable to transfer this energy to a second luminescent molecule with CP properties (hereafter CP molecule) as a dopant and as an emitter enabling the emission of a circularly polarized light with a high polarization rate.

The invention differs from the prior art in that it uses a TADF molecule as a host molecule without any CP properties and a CP molecule as a dopant without any TADF properties.

This new approach makes it possible to reach a higher level of polarization of the light emitted by the composition than the levels reached by the prior art.

Other optional and non-limiting features are as follows.

The TADF molecule may exhibit a singlet state energy level and a triplet state energy level and the CP molecule a singlet state energy level lower than the singlet state and triplet state energy levels of the TADF molecule.

The CP molecule may have an absorption spectrum and the TADF molecule a luminescence spectrum overlapping the absorption spectrum of the CP molecule.

The composition may exhibit a luminescence polarization measured through the $g_{lum}$ value which is different from 0. Preferably, the $|g_{lum}|$ absolute value is higher than $5\times10^{-4}$, still preferably higher than $1\times10^{-3}$ or even higher than $1\times10^{-2}$. This value is taken at the wavelength where a maximum of luminescence intensity is measured.

The composition may exhibit a TADF quantum yield of 1% or higher. Preferably, the TADF quantum yield is higher than 5%. It is preferably lower than 50%. For example, any of the following figures can serve as a lower range value or a higher range value: 10%, 20%, 30% and 40%.

The composition may exhibit a luminescence quantum yield of 0.10 or higher. Preferably, the luminescence quantum yield is higher than 5%. It is preferably lower than 100%. For example, any of the following figures can serve as a lower range value or a higher range value: 10%, 15%, 20%, 30%, 50%, 75%, and 95%.

The CP molecule may be a chiral molecule, such as a helicene derivative, a helicenoid compound, a biarylic system, a molecule with planar chirality (e.g. paracyclophane derivatives).

The CP molecule may be for example a carbo[6]helicene derivate (hereafter H6) with the general formula Chem. 1:

[Chem. 1]

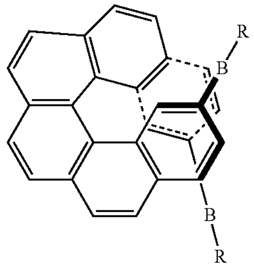

In formula Chem. 1, B, a linker, may be one of the following chemical groups represented in Chem. 2:

[Chem. 2]

A:  ;

(ethyne-1,2-diyl)

B: 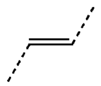

(E-ethene;-1,2-diyl);

C: 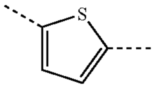 ;

(tiophene-2,5-diyl)

D: 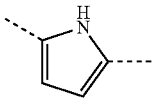 ;

(pyrole-2,5-diyl)

E: 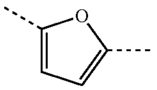 ;

(furane-2,5-diyl)

E: 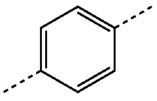 ;

(benzene-1,4-diyl)

In formula Chem. 1, B may also be a combination of two of the chemical groups of Chem. 2, for example a combination of chemical groups A and any one of the other chemical groups of Chem. 2, preferably in such case chemical group A bonds to the helicene group of Chem. 1. In particular, B may be a chemical group A of Chem. 2 bonded to the chemical group F of Chem. 2.

In formula Chem. 1, R may be one of the following chemical groups depicted in Chem. 3:

[Chem. 3]

G: 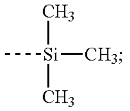

(trimethylsilyle)

H: 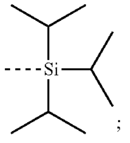

(triisopropylsilyle)

I: ----C≡N;

(cyanyle)

J: ----$NH_2$;

(aminyle)

K: 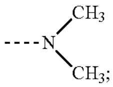

(dimethylaminyle)

L: 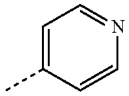

(4-pyridinyle)

Preferably still, the H6 has one of the following formulae Chem. 4 and Chem. 5, Chem. 6, Chem. 7, Chem. 8, Chem. 9 and Chem. 10.

[Chem. 4]

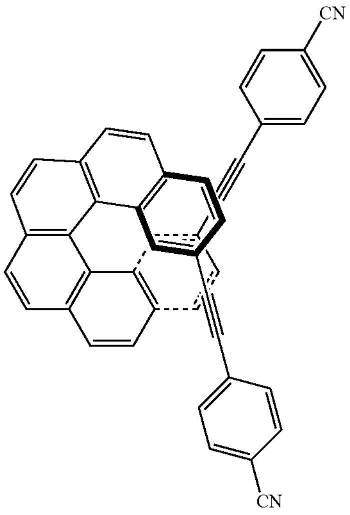

4,4'-(hexahelicene-2,15-diylbis(ethyne-2,1-diyl))dibenzonitrile, hereafter $H6(CN)_2$.

[Chem. 5]

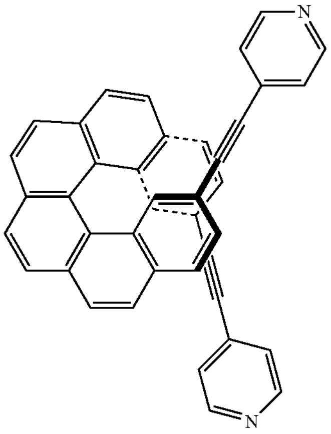

4,4'-(hexahelicene-2,15-diylbis(ethyne-2,1-diyl))dipyridine, hereafter $H6(Py)_2$.

[Chem. 6]

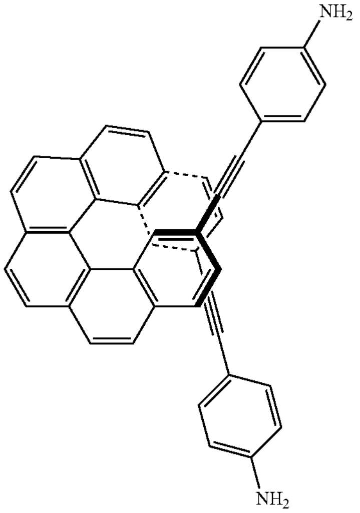

4,4'-(hexahelicene-2,15-diylbis(ethyne-2,1-diyl))dianiline, hereafter $H6(NH_2)_2$.

[Chem. 7]

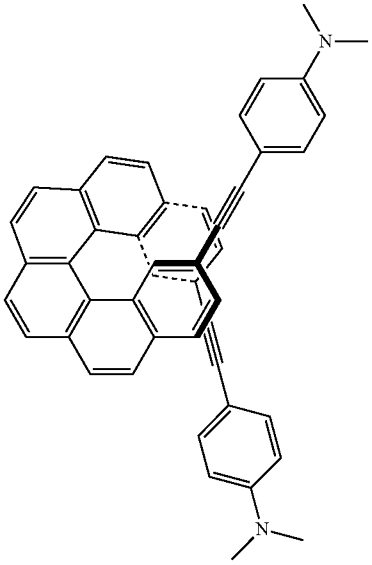

4,4'-(hexahelicene-2,15-diylbis(ethyne-2,1-diyl))di(N,N-dimethylaniline), hereafter $H6(NMe_2)_2$.

[Chem. 8]

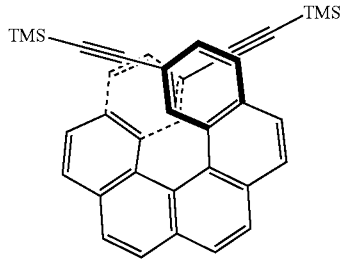

4,4'-(hexahelicene-2,15-diylbis(ethyne-2,1-diyl))di(trimethylsilane), hereafter $H6(TMS)_2$.

[Chem. 9]

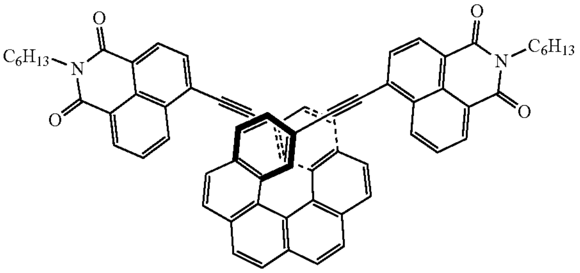

4,4'-(hexahelicene-2,15-diylbis(ethyne-2,1-diyl))di(N-hexyl-1,8-naphthalimide), hereafter $H6(NPh)_2$.

[Chem. 10]

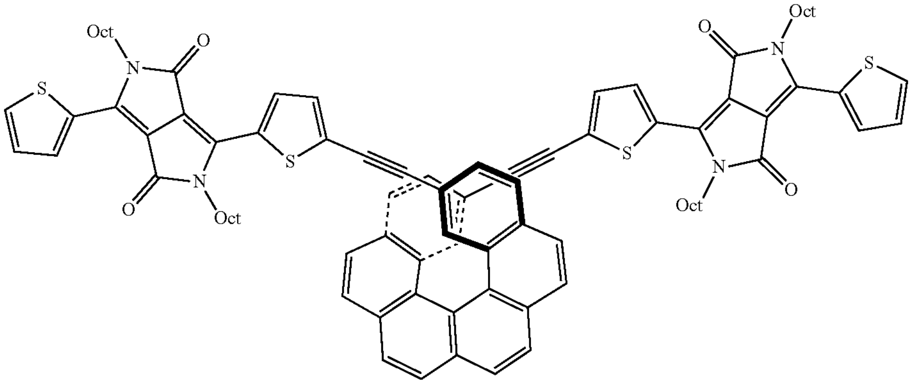

4,4'-(hexahelicene-2,15-diylbis(ethyne-2,1-diyl))di(2,5-N-octyl-3,6-di-2-thienyl-pyrrolo[3,4-c]pyrrole-1,4-dione), hereafter $H6(DPP)_2$.

The H6 may exhibit a P or an M configuration.

The TADF molecule may be an achiral molecule. In particular, the TADF molecule may have one of formulae Chem. 11, Chem. 12 and Chem. 13.

[Chem. 11]

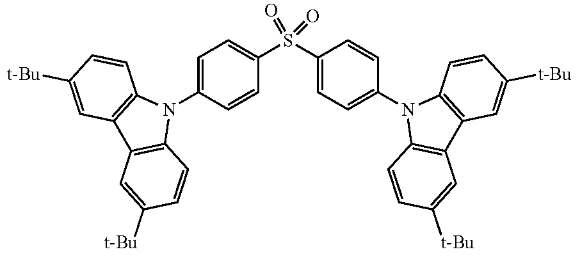

9,9'-(sulfonylbis(4,1-phenylene))bis(3,6-di-tert-butyl-9H-carbazole, hereafter dt-BuCbzSulfone.

[Chem. 12]

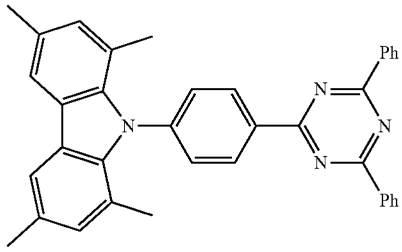

9-(4-(4,6-diphenyl-1,3,5-triazin-2-yl)phenyl)-1,3,6,8-tetramethyl-9H-carbazole, hereafter Cbz-TRZ2.

[Chem. 13]

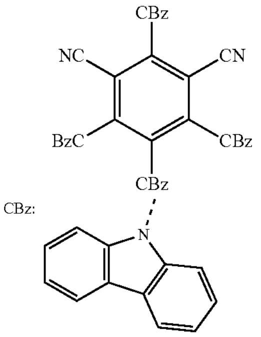

2,4,5,6-tetra(9H-carbazol-9-yl)isophthalonitrile, hereafter 4-CbzIPN.

The active light-emitting layer composition may have one of the following combinations of TADF molecule and CP molecule:

dt-BuCbzSulfone and $H6(CN)_2$;

Cbz-TRZ2 and $H6(NPh)_2$; and

4-CbzIPN and $H6(DPP)_2$.

However, the invention is not limited to these combinations and any other combination is also possible:

dt-BuCbzSulfone with $H6(NPh)_2$ or $H6(DPP)_2$;

Cbz-TRZ2 with $H6(CN)_2$ or $H6(DPP)_2$;

4-CbzIPN with $H6(CN)_2$ or $H6(NPh)_2$.

The CP molecule can be at an amount of 1 to 30%, preferably 1 to 20%, 1 to 10% or 1 to 5%, by mole of the TADF molecule.

The composition may further comprise an electrically conducting matrix for the conduction of electric charge through the light-emitting layer. In such case, the amount of TADF molecule is preferably 1 to 30%, preferably 1 to 20%, 1 to 10% or 1 to 5%, by mole of the electrically conducting matrix.

The summed amount of both the TADF molecule and CP molecule is preferably from 1% to 40%, 5% to 30%, of the total weight of the composition.

The invention also provides a light-emitting device having the active light-emitting layer made of an active light-emitting layer composition as described above. The light-emitting device may be an OLED displaying device.

BRIEF DESCRIPTION OF DRAWINGS

Other features, details and advantages will be shown in the following detailed description and on the figures, on which.

DETAILED DESCRIPTION

The present invention is now further described with reference to the accompanying FIGS. 1 to 7. Throughout this disclosure, when there is a discrepancy between the name of a chemical compound and its developed structure, precedence should be given to the developed structure (without consideration of its configuration unless stated otherwise).

The principle of the present invention is based on the energy transfer occurring from the TADF molecule to the CP molecule; the TADF molecule being the host and the CP molecule being an emitter, which ultimately emits circularly polarized emission.

Figure 1:
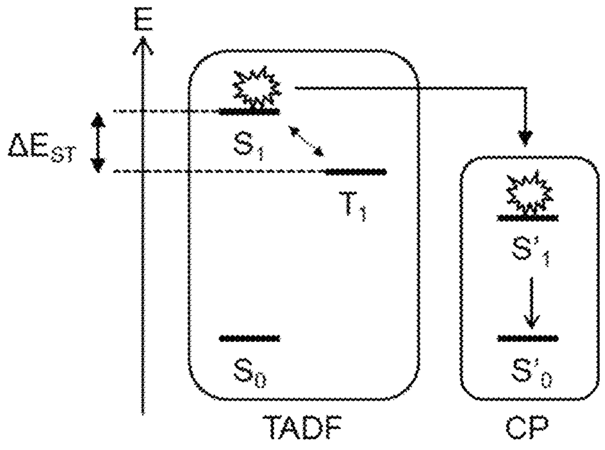
FIG. 1 is an illustration showing the principle behind the present invention, notably the transfer of energy from the singlet energy level of the TADF molecule to the singlet energy level of the CP molecule.

More precisely, as shown in FIG. 1, upon electrical or optical excitation of the TADF molecule, its excited-state will be in equilibrium between the singlet $S_1$ and triplet $T_1$ spin configurations to some extent (through intersystem crossing and reverse intersystem crossing processes), which is governed by the energy gap between these two states $\Delta E_{ST}$. During that period of time, the equilibrium is shifted toward the singlet state $S_1$ since its deactivation through fluorescence emission occurs much faster than phosphorescence emission from the triplet state $T_1$ (rates being of the order of ns and μs, respectively). Finally, there are two fluorescence emission processes, one occurring directly from the singlet state $S_1$ (prompt fluorescence, in ns timescale) and another one that delayed in time (delayed fluorescence, in μs timescale) due to the formation of the singlet-triplet excited states equilibrium. This equilibrium is very important for instance in OLEDs since it can yield a theoretical internal quantum efficiency of 100%, in comparison to the maximum theoretical internal quantum efficiency of 25% for pure fluorescence emitters.

The present authors found out that doping a solid film of a TADF molecule with a luminescence molecule with an excited state $S'_1$ lower in energy than the singlet and triplet states of the TADF molecule, its deactivation may occur through a different pathway than the prompt and delayed fluorescences; that is an energy transfer from the singlet state $S_1$ of the TADF molecule to the excited state $S'_1$ of the luminescence molecule with lowest energy. The luminescence molecule eventually emits light when it goes back to its ground state $S'_0$. In the present case, the luminescent molecule exhibits circular polarization properties, for example when it is a chiral molecule, and it emits a circularly polarized light upon optical and/or electrical excitation of the TADF molecule.

The 'doping ratio' is the proportion of dopant present in a composition, by moles, with reference to the TADF host. This bimolecular system can be also placed in an organic matrix to form a ternary active layer (here again the 'doping ratio' will be based on the proportion of the chiral emitter and the TADF host, by moles, regarding the TADF host).

In order to ensure a more efficient energy transfer, the luminescence spectrum of the TADF molecule should overlap with the absorption spectrum of the CP molecule. Moreover, within the emitting layer of an OLED device, the ratio of the CP molecule with regard to the TADF molecule should be as low as possible to avoid direct carrier trapping. This is why it is used as a dopant and not as a main component of the composition. However, it should not be too low to ensure sufficient energy transfer and no residual TADF emission. Accordingly, the optimum ratio of CP molecule to TADF molecule may change and the person skilled in the art would be able to optimize the ratio for different combinations of TADF molecule and CP molecule.

Methods

NMR spectrum measurements. $^1H$ and $^{13}C$ NMR spectra were recorded at room temperature on an A VANCE III 400 BRUKER or an AVANCE 1500 BRUKER. Chemical shifts δ are given in ppm and coupling constants J in Hz. Chemical shifts for $^1H$ NMR spectra are referenced relative to residual protium in the deuterated solvent (δ=7.26 ppm, $CDCl_3$). $^{13}C$ shifts are referenced to $CDCl_3$ peaks at δ=77.16 ppm.

Mass-spectrometry measurements. High-resolution mass (HR-MS) determinations were performed at CRMPO on a Bruker MaXis 4G by ASAP (+ or −) or ESI and MALDI with $CH_2Cl_2$ as solvent techniques. Experimental and calculated masses are given with consideration of the mass of the electron.

UV spectrum measurements. UV-Visible (UV-vis, in M−1 cm−1) absorption spectra were recorded on a UV-2401PC Shimadzu spectrophotometer.

Fluorescence spectrum measurements. Fluorescence spectra were recorded on a FL 920 Edinburgh fluorimeter.

Fluorescence quantum yield measurements. Fluorescence quantum yields in diluted solution (in dichloromethane) are measured using the following equation Math. 1; where the subscripts "ST" and "X" denote "standard" and "sample" respectively, Φ is the fluorescence quantum yield, Grad is the gradient from the plot of integrated fluorescence intensity vs. absorbance, and η is the refractive index of the solvent. Reference for fluorescence quantum yields used herein are quinine sulfate in 0.5 M sulfuric acid and rhodamine 6G (Excitation of reference and sample compounds was performed at the same wavelength):

$$\Phi_X = \Phi_{ST}\left(\frac{Grad_X}{Grad_{ST}}\right)\left(\frac{\eta_X^2}{\eta_{ST}^2}\right) \quad \text{[Math. 1]}$$

Fluorescence quantum yields in solid state are measured using the following equation Math. 2; where "R" and "X" stand for reference and sample, respectively. A(λ) is the absorbance at the excitation wavelength λ, n is the refractive index, and D is the integrated intensity. The luminescence quantum yields were measured relative to rhodamine 6G in ethanol ($\Phi_R$=0.91). Excitation of reference and sample compounds was performed at the same wavelength $$\frac{\Phi_X}{\Phi_{ST}} = \left(\frac{A_R(\lambda)}{A_X(\lambda)}\right)\left(\frac{n_X^2}{n_R^2}\right)\left(\frac{D_X}{D_R}\right) \quad \text{[Math. 2]}$$

TADF quantum yield measurements. The TADF quantum yields are determined by using fluorescence quantum yields determined in the presence ($\Phi_{Ox}$) and absence ($\Phi_{Ar}$) of oxygen; assuming that delayed fluorescence is negligible in the presence of oxygen (see Math. 3).

$$\Phi_X=\Phi_{TADF}+\Phi_{CP}=\Phi_{A1}$$

$$\Phi_{CP}=\Phi_{O1}$$

$$\Phi_{TADF}=\Phi_{A1} \ldots \Phi_{Ox} \quad \text{[Math. 3]}$$

$\Phi_{Ox}$ and $\Phi_{Ar}$ are determined by using total photoluminescence quantum efficiency and are measured using a Hamamatsu C9920-03 integrating sphere.

Luminescence dissymmetry factor measurements. The luminescence dissymmetry factor $g_{lum}$ is representative of the circular polarization. It is measured by formula Math. 4, where $I_L$ and $I_R$ refer to the left-handed and right-handed polarized light intensities, respectively.

$$g_{lum} = \frac{I_L - I_R}{I_L + I_R} \quad \text{[Math. 4]}$$

Values of $g_{lum}$ range from −2 to +2 in which a negative value means a right-handed CP and a positive value a left-handed CP. The value of 0 means absence of CP, whereas an absolute value of 2 means completely circularly polarized light.

These measurements were performed using a CPL spectrometer (JASCO Company). The samples were dissolved in dichloromethane and excited using a 90° geometry with a Xenon ozone-free lamp 150 W LS. The following parameters were used: emission slit width≈2 mm, integration time=4 sec, scan speed=50 nm/min, accumulations=5. Excitation of the samples was performed at 350 nm. Further details can be found in Abbate et al., 2016 [1].

Examples 1 and 2: 2,15-bisethynylhexahelicene $H6(H)_2$ and 4,4'-(hexahelicene-2,15-diylbis(ethyne-2,1-diyl))di(trimethylsilane) $H6(TMS)_2$ P-$H6(H)_2$ of formula Chem. 14 and $H6(TMS)_2$ were prepared following the strategy previously reported by Crassous, J et al. (2018) [2].

[Chem. 14]

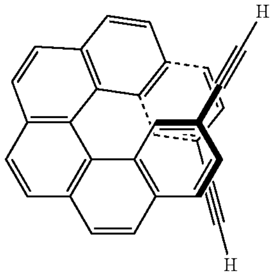

Example 2: 4,4'-(hexahelicene-2,15-diylbis(ethyne-2,1-diyl))dibenzonitrile $H6(CN)_2$ P-$H6(CN)_2$ was synthesized as illustrated below by Chem. 15. First P-$H6(H)_2$ (50 mg, 0.13 mmol) and 4-bromobenzonitrile (71 mg, 0.39 mmol) were placed in an oven-dried flask of 25 mL under argon. Then 4 mL of dry toluene and 1 mL of dry triethylamine ($Et_3N$) were added and the resulting solution was freed from oxygen by bubbling argon for 1 hour. Tetrakis(triphenylphosphine)palladium(0) ($Pd(PPh_3)_4$) (15 mg, 0.013 mmol) and copper(I) iodide (CuI) (4.9 mg, 0.026 mmol) were added and the solution was refluxed for 3 hours. After cooling down to room temperature, the solution was passed through a short silica plug (dichloromethane, $CH_2Cl_2$). The crude mixture was further purified by column chromatography on silica (8/2 Heptane/$CH_2Cl_2$ eluent system) to yield P-$H6(CN)_2$ (63.9 mg, 85%) as a yellow solid.

[Chem. 15]

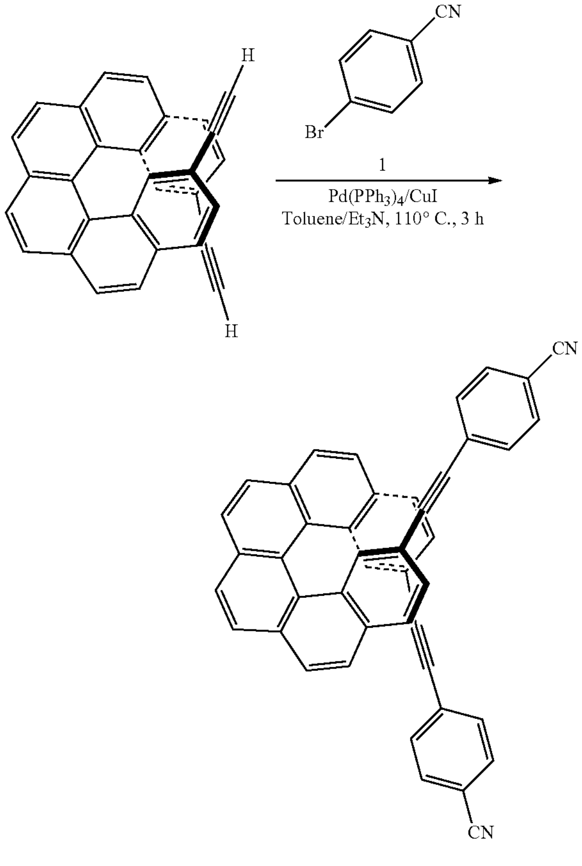

$^1$H NMR (300 MHz, Methylene Chloride-$d_2$) δ 8.19-8.07 (m, 6H), 8.04-7.99 (d, J=8.6 Hz, 2H), 7.90-7.88 (s, 1H), 7.87-7.83 (dd, J=3.1, 2.0 Hz, 3H), 7.69-7.67 (d, J=1.3 Hz, 2H), 7.67-7.63 (d, J=1.3 Hz, 2H), 7.47-7.44 (d, J=1.2 Hz, 2H), 7.44-7.42 (d, J=1.6 Hz, 3H), 7.41-7.39 (d, J=1.5 Hz, 1H).

$^{13}$C NMR (75 MHz, Methylene Chloride-$d_2$) δ 133.6, 133.2, 132.2, 132.1, 132.11, 132.1-132.0, 132.0-131.9, 131.8-131.7, 129.2-128.9, 128.2-128.0, 127.9-127.8, 127.9-127.8, 127.8-127.7, 127.7-127.6, 127.5-127.4, 127.4-127.3, 127.0-126.9, 124.0-123.6, 118.5-118.4, 118.4-118.3, 111.5-111.2, 94.3-93.1, 88.2-86.0.

HR-MS Ultraflex III, MALDI, 370° C.; ion $[M]^+$, $C_{44}H_{22}N_2$, m/z calculated 578.17775, m/z experimental 578.182 (Δ=7 ppm).

Example 3: 4,4'-(hexahelicene-2,15-diylbis(ethyne-2,1-diyl))dipyridine $H6(Py)_2$ P-$H6(Py)_2$ was synthesized as illustrated below by Chem. 16. A mixture of P-$H6(H)_2$ (50 mg, 0.13 mmol) and 4-bromopyridine hydrochloride (75.8 mg, 0.39 mmol) were placed in an oven-dried flask of 25 mL under argon. Then 5 mL of dry propylamine was added and the resulting solution was freed from oxygen by bubbling argon for 1 hour. $Pd(PPh_3)_4$ (15 mg, 0.013 mmol) and CuI (4.9 mg, 0.026 mmol) were added and the solution was refluxed for 3 hours. After cooling down to room temperature, the solution was passed through a short silica plug ($CH_2Cl_2$). The crude mixture was further purified by column chromatography on silica (5/5 Heptane/$CH_2Cl_2$ eluent system) to yield P-$H6(Py)_2$ (44.8 mg, 65%) as a yellow solid.

[Chem. 16]

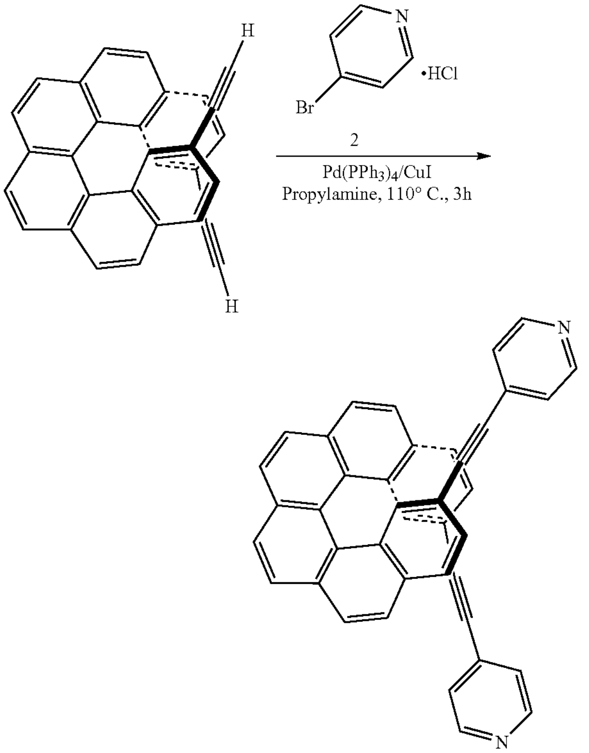

$^1H$ NMR (400 MHz, Methylene Chloride-$d_2$) δ 8.61-8.59 (d, J=1.7 Hz, 2H), 8.59-8.56 (d, J=1.7 Hz, 2H), 8.16-8.12 (d, J=8.2 Hz, 2H), 8.12-8.10 (d, J=1.6 Hz, 2H), 8.10-8.06 (d, J=2.0 Hz, 2H), 8.05-8.02 (s, 1H), 8.02-8.00 (s, 1H), 7.91-7.89 (s, 1H), 7.88-7.87 (s, 1H), 7.87-7.83 (m, 2H), 7.44-7.43 (d, J=1.6 Hz, 1H), 7.42-7.41 (d, J=1.6 Hz, 1H), 7.24-7.22 (d, J=1.7 Hz, 2H), 7.22-7.20 (d, J=1.6 Hz, 2H).

$^{13}C$ NMR (101 MHz, Methylene Chloride-$d_2$) δ 149.9, 149.6, 133.6, 133.3, 132.4, 132.2, 132.2, 132.1, 132.0, 131.8, 131.6, 131.0, 129.1, 129.0, 127.9, 127.9, 127.9, 127.9, 127.9, 127.8, 127.7, 127.6, 127.5, 127.5, 127.4, 127.4, 127.1, 126.8, 125.5, 124.9, 124.0, 123.4, 118.4, 118.0, 94.3, 92.0, 87.1, 84.2.

HR-MS Ultraflex III, MALDI, 370° C.; ion $[M+H]^+$, $C_{40}H_{23}N_2$, m/z calculated 531.18557, m/z experimental 531.182 (Δ=7 ppm).

Example 4: 4,4'-(hexahelicene-2,15-diylbis(ethyne-2,1-diyl))dianiline $H6(NH_2)_2$ P-$H6(NH_2)_2$ was synthesized as illustrated below by Chem. 17. P-$H6(H)_2$ (50 mg, 0.13 mmol) and 4-iodoaniline (126 mg, 0.575 mmol) were placed in an oven-dried flask of 25 mL under argon. Then 5 mL of dry propylamine was added and the resulting solution was freed from oxygen by bubbling argon for 1 hour. Pd(PPh3)4 (15 mg, 0.013 mmol) and CuI (4.9 mg, 0.026 mmol) were added and the solution was refluxed for 3 hours. After cooling down to room temperature, the solution was passed through a short silica plug ($CH_2Cl_2$). The crude mixture was further purified by column chromatography on silica (5/5Heptane/$CH_2Cl_2$ eluent system) to yield P-$H6(NH_2)_2$ (47.2 mg, 65%) as a yellow solid.

$^1H$ NMR (400 MHz, Methylene Chloride-$d_2$) δ 8.10-7.94 (m, 8H), 7.85-7.78 (d, J=8.3 Hz, 2H), 7.75-7.72 (m, 2H), 7.37-7.35 (d, J=1.6 Hz, 1H), 7.34-7.33 (d, J=1.6 Hz, 1H), 7.14-7.13 (d, J=2.0 Hz, 2H), 7.12-7.11 (d, J=2.0 Hz, 2H), 6.64-6.62 (d, J=2.0 Hz, 2H), 6.62-6.59 (d, J=2.0 Hz, 2H), 3.93-3.85 (s, 4H).

$^{13}C$ NMR (101 MHz, Methylene Chloride-$d_2$) δ 148.1, 146.2, 133.6, 133.3, 132.9, 132.7, 132.2, 131.8, 131.6, 131.4, 131.3, 131.1, 129.6, 129.3, 128.2, 127.9, 127.8, 127.7, 127.7, 127.6, 127.5, 127.4, 127.3, 127.2, 127.1, 126.9, 124.5, 123.6, 120.7, 119.9, 115.3, 114.3, 112.9, 111.9, 90.4, 88.7, 88.1, 86.7.

HR-MS Ultraflex III, MALDI, 370° C.; ion $[M]^+$, $C_{42}H_{26}N_2$, m/z calculated 558.20905, m/z experimental 558.207 (Δ=4 ppm).

Example 5: 4,4'-(hexahelicene-2,15-diylbis(ethyne-2,1-diyl))di(N,N-dimethylaniline) $H6(NMe_2)_2$ P-$H6(NMe_2)_2$ was synthesized as illustrated below by Chem. 17 from $H6(NH_2)_2$ of Example 4. To a solution of P-$H6(NH_2)_2$ (30 mg, 0.054 mmol) dissolved in 5 mL of tetrahydrofurane (THF) in a round-bottomed flask, formaldehyde (0.04 mL, 0.13 mmol) was added dropwise to the flask. The mixture was stirred for 15 min at room temperature under argon. Then, sodium cyanoborohydride ($NaBH_3CN$) (34 mg, 0.54 mmol) was introduced directly into the solution. The mixture was stirred for 15 min at room temperature a second time. Acetic acid (1 mL) was added to stop the reaction and the solution was stirred for 2 h at room temperature. After addition of water and dichloromethane (25 mL each), the organic layer was separated and the aqueous layer was extracted with dichloromethane. All organic layers were gathered, dried over $mgSO_4$ and the solvent was evaporated. The crude product was purified by a plug of silica and washed by dichloromethane and the desired product P-$H6(NMe_2)_2$ was obtained as a yellow solid (14.9 mg, 45%).

[Chem. 17]

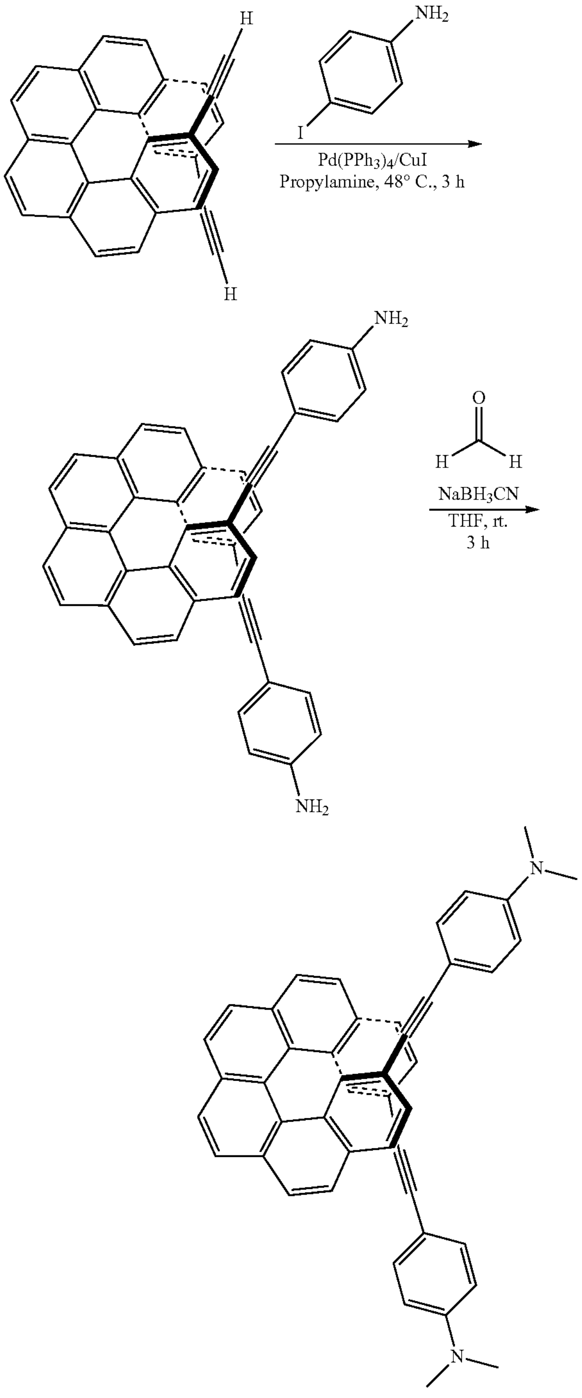

$^1H$ NMR (400 MHz, Methylene Chloride-$d_2$) δ 8.16-7.97 (m, 8H), 7.91-7.81 (d, J=8.3 Hz, 2H), 7.81-7.74 (d, J=1.5 Hz, 2H), 7.43-7.34 (dd, J=8.2, 1.6 Hz, 2H), 7.26-7.24 (d, J=2.1 Hz, 2H), 7.23-7.21 (d, J=2.0 Hz, 2H), 6.73-6.69 (d, J=2.1 Hz, 2H), 6.69-6.66 (s, 2H), 3.20-2.52 (s, 12H).

$^{13}C$ NMR (126 MHz, Methylene Chloride-$d_2$) δ 150.6, 149.5, 133.4, 133.1, 132.5, 132.3, 131.9, 131.7, 131.3, 131.2, 131.0, 130.7, 129.5, 129.3, 127.9, 127.8, 127.6, 127.6, 127.5, 127.4, 127.3-127.2 (d, J=3.7 Hz), 127.2, 127.1, 126.8, 126.7, 124.1, 123.8, 120.6, 120.3, 112.7, 110.6, 110.5, 109.4, 90.4, 89.1, 88.2, 86.4, 40.5, 39.2.

HR-MS Ultraflex III, ESI, 370° C.; ion $[M+H]^+$, $C_{46}H_{35}N_2$, m/z calculated 615.27947, m/z experimental 615.2796 (Δ=0 ppm).

Example 6

Results of measurements of luminescence quantum yield in dichloromethane at 298 K and luminescence dissymmetry factor for Examples 1 to 5 above are summed up in the following Table 1 (in the table "yEx" stands for "y×$10^x$").

TABLE 1

| Compounds | $\Phi_X$ (%) | $\lvert g_{lum} \rvert$<br>λ(nm) |
|---|---|---|
| $H6(TMS)_2$ | 6 | 1.1E−2<br>421 |
| $H6(CN)_2$ | 9 | 2.7E−2<br>426 |
| $H6(Py)_2$ | 6 | 2.5E−2<br>429 |
| $H6(NH_2)_2$ | 16 | 2.5E−2<br>430 |
| $H6(NMe_2)_2$ | 41 | 5.2E−3<br>500 |

Example 7

An illustration of the present invention is provided here. In this example, the active light-emitting layer composition comprises as a TADF molecule dt-BuCbzSulfone and as a CP molecule $H6(CN)_2$. TADF molecule dt-BuCbzSulfone was developed in 2012 by Adachi et al. [3] whereas $H6(CN)_2$ has been first synthetized and developed by the applicant to their knowledge.

Figure 2:
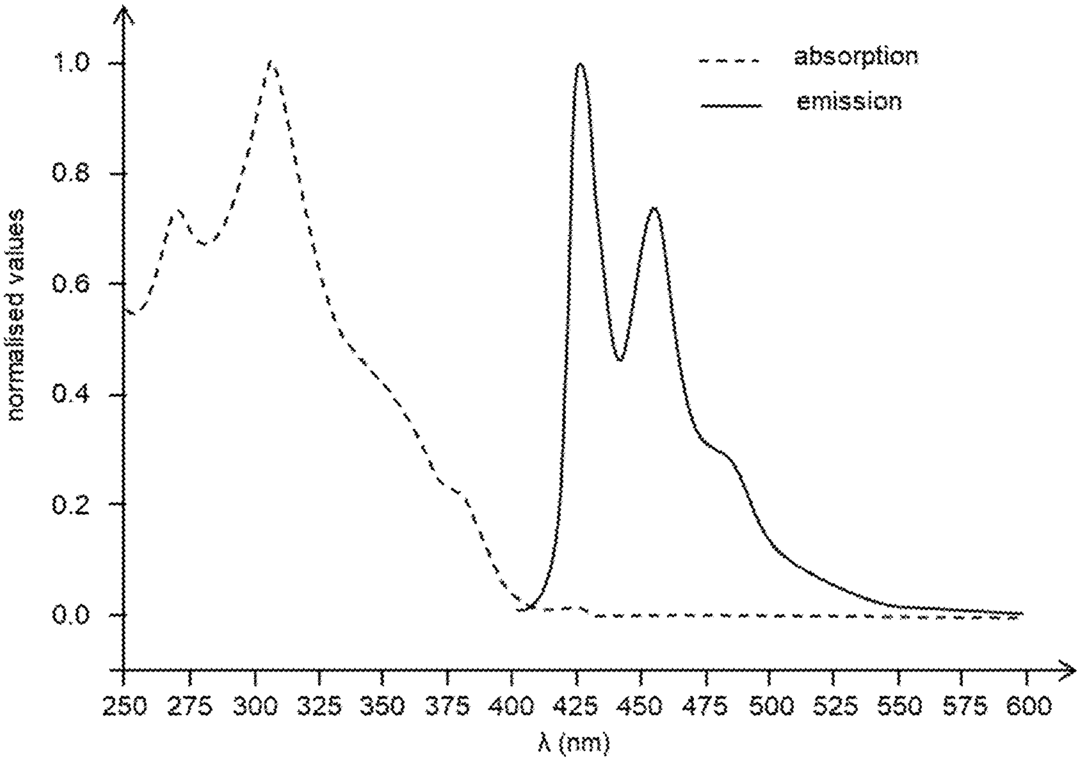
FIG. 2 is a graph showing the absorption spectrum (dotted line) and the emission spectrum (solid line) of $H6(CN)_2$ between 250 nm and 600 nm recorded in dichloromethane solvent at room temperature, the values being normalized so that the highest peak has a value of 1.
Figure 3:
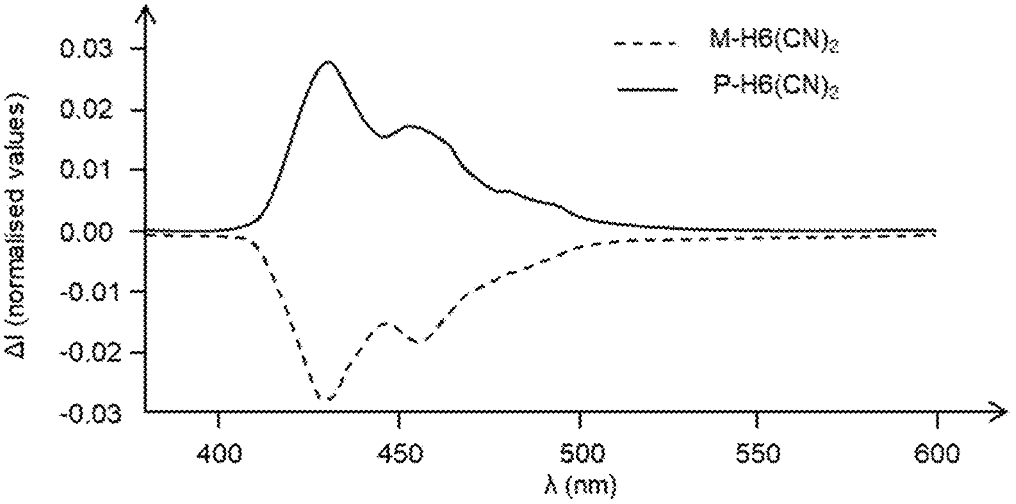
FIG. 3 is a graph showing the intensity difference ΔI between left-handed emitted light and right-handed emitted light of M-$H6(CN)_2$ (dotted line) and P-$H6(CN)_2$ (solid line) approximately between 400 nm and 600 nm recorded in dichloromethane solvent at room temperature. The values are normalized so that the highest peak $I_{max}$ of the total emission spectrum has a value of 2. In such a situation, the value of ΔI at the wavelength of $I_{max}$ is the $g_{lum}$ value at that wavelength.
Figure 4:
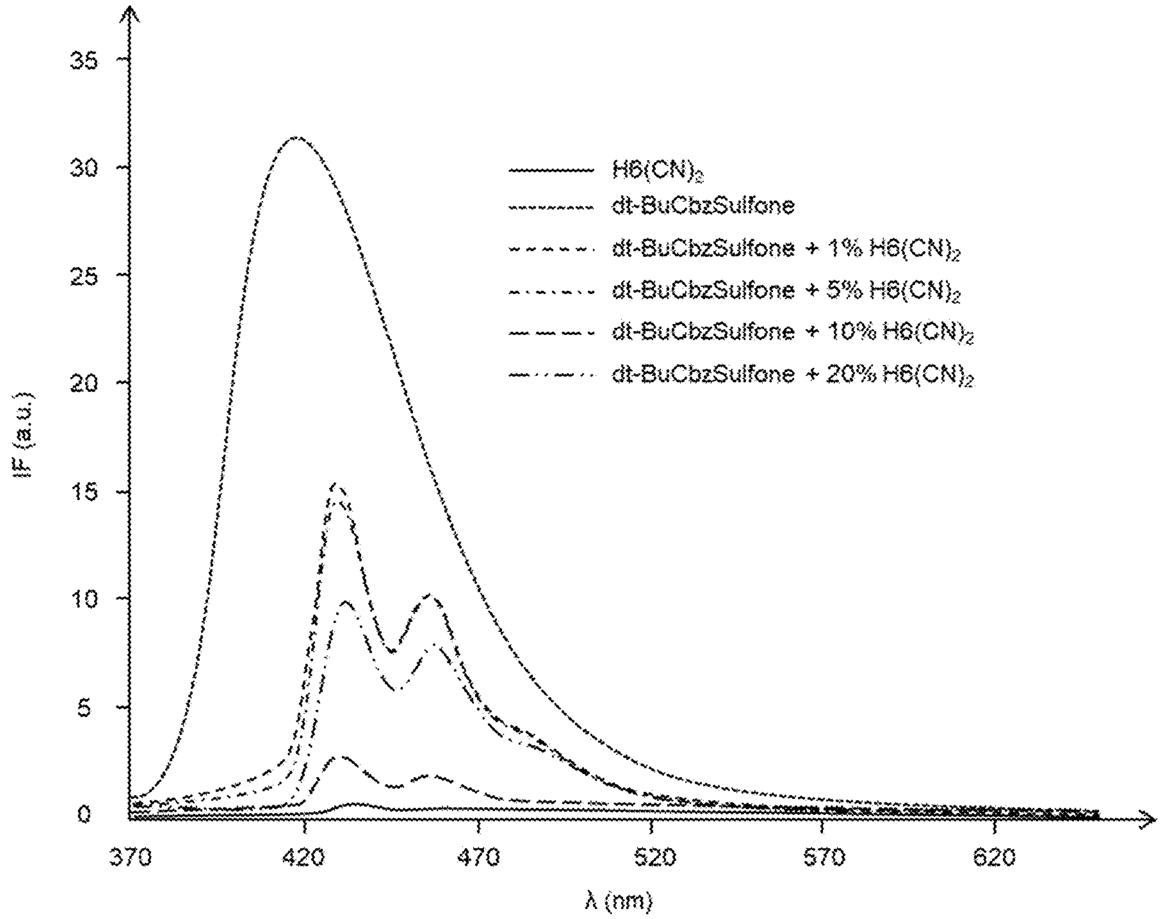
FIG. 4 is a graph showing the emission spectra between 370 nm and 370 nm of $H6(CN)_2$ alone, dt-BuCbzSulfone alone, and a composition consisting of dt-BuCbzSulfone and $H6(CN)_2$ at 1, 5, 10 and 20 mol. % of the amount of dt-BuCbzSulfone, recorded on films at room temperature.
Figure 5:
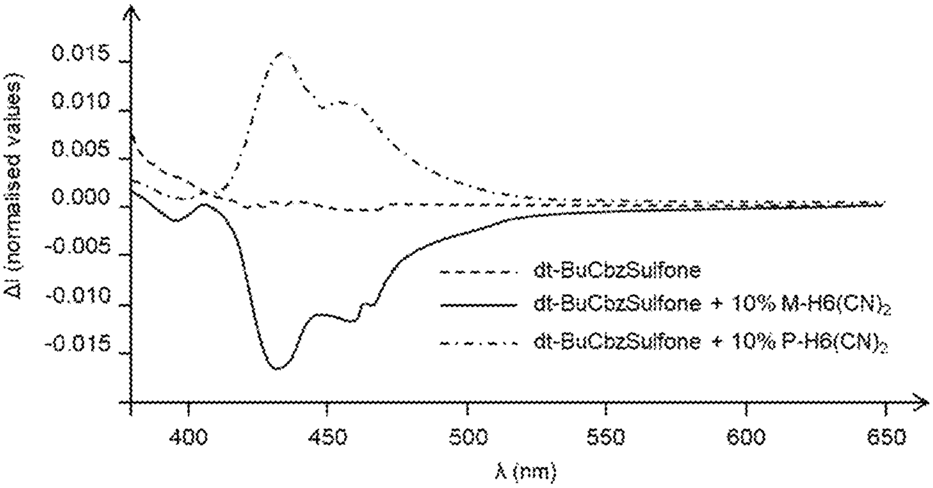
FIG. 5 is a graph showing the intensity difference ΔI between left-handed emitted light and right-handed emitted light of BuCbzSulfone alone, and a composition consisting of dt-BuCbzSulfone and M-$H6(CN)_2$ or P-$H6(CN)_2$ at 10 mol. % of the amount of dt-BuCbzSulfone, approximately between 400 nm and 650 nm, recorded on films at room temperature. The values correspond to the normalized value of emission intensity in FIG. 5. In such situation, the value of ΔI at the wavelength of the highest peak in the emission spectrum is the $g_{lum}$ value at that wavelength.

$H6(CN)_2$ presents a singlet energy level at 2.99 eV at 415 nm and 2.92 eV at 425 nm. Photophysical and chiroptical properties of $H6(CN)_2$ are shown in FIGS. 2 and 3.

Table 2 below shows normalized absorption values and Table 3 normalized emission values between 250 nm and 600 nm and correspond to FIG. 2. In FIG. 2, the normalized absorption is represented in dotted line whereas the normalized emission is represented as a solid line. The highest peak is normalized to a value of 1 and the other are proportional thereto.

TABLE 2

| λ (nm) | I (a.u.) |
|---|---|
| 250 | 0.553 |
| 255 | 0.556 |
| 260 | 0.599 |
| 265 | 0.678 |
| 270 | 0.733 |
| 275 | 0.697 |
| 280 | 0.672 |
| 285 | 0.687 |
| 290 | 0.727 |
| 295 | 0.784 |
| 300 | 0.890 |
| 305 | 1.000 |
| 310 | 0.955 |
| 315 | 0.846 |
| 320 | 0.716 |
| 325 | 0.637 |
| 330 | 0.567 |
| 335 | 0.510 |
| 340 | 0.475 |
| 345 | 0.452 |
| 350 | 0.423 |
| 355 | 0.392 |
| 360 | 0.355 |
| 365 | 0.316 |
| 370 | 0.267 |
| 375 | 0.239 |
| 380 | 0.223 |
| 385 | 0.186 |
| 390 | 0.127 |
| 395 | 0.072 |
| 400 | 0.046 |
| 405 | 0.026 |
| 410 | 0.011 |
| 415 | 0.009 |
| 420 | 0.011 |
| 425 | 0.012 |
| 430 | 0.005 |
| 435 | 0.001 |
| 440 | 0.001 |
| 445 | 0.003 |
| 450 | 0.004 |
| 455 | 0.005 |
| 460 | 0.004 |
| 465 | 0.003 |
| 470 | 0.001 |
| 475 | 0.000 |
| 480 | 0.000 |
| 485 | 0.000 |
| 490 | 0.000 |
| 495 | 0.000 |
| 500 | 0.000 |
| 505 | 0.001 |
| 510 | 0.001 |
| 515 | 0.000 |
| 520 | 0.001 |
| 525 | 0.001 |
| 530 | 0.000 |
| 535 | 0.000 |
| 540 | 0.000 |
| 545 | 0.000 |
| 550 | 0.000 |
| 555 | 0.000 |
| 560 | 0.000 |
| 565 | 0.000 |
| 570 | 0.000 |
| 575 | 0.000 |
| 580 | 0.000 |
| 585 | 0.000 |
| 590 | 0.000 |
| 595 | 0.000 |
| 600 | 0.000 |

TABLE 3

| λ (nm) | I (a.u.) |
|---|---|
| 402 | 0.008 |
| 404 | 0.011 |
| 406 | 0.013 |
| 408 | 0.018 |
| 410 | 0.024 |
| 412 | 0.038 |
| 414 | 0.065 |
| 416 | 0.117 |
| 418 | 0.223 |
| 420 | 0.413 |
| 422 | 0.663 |
| 424 | 0.895 |
| 426 | 1.000 |

TABLE 3-continued

| λ (nm) | I (a.u.) |
|---|---|
| 428 | 0.994 |
| 430 | 0.916 |
| 432 | 0.803 |
| 434 | 0.699 |
| 436 | 0.604 |
| 438 | 0.528 |
| 440 | 0.478 |
| 442 | 0.460 |
| 444 | 0.479 |
| 446 | 0.534 |
| 448 | 0.586 |
| 450 | 0.656 |
| 452 | 0.710 |
| 454 | 0.739 |
| 456 | 0.734 |
| 458 | 0.687 |
| 460 | 0.620 |
| 462 | 0.549 |
| 464 | 0.485 |
| 466 | 0.428 |
| 468 | 0.389 |
| 470 | 0.355 |
| 472 | 0.334 |
| 474 | 0.317 |
| 476 | 0.305 |
| 478 | 0.300 |
| 480 | 0.294 |
| 482 | 0.290 |
| 484 | 0.282 |
| 486 | 0.271 |
| 488 | 0.252 |
| 490 | 0.232 |
| 492 | 0.212 |
| 494 | 0.189 |
| 496 | 0.172 |
| 498 | 0.155 |
| 500 | 0.140 |
| 502 | 0.127 |
| 504 | 0.116 |
| 506 | 0.108 |
| 508 | 0.101 |
| 510 | 0.093 |
| 512 | 0.088 |
| 514 | 0.082 |
| 516 | 0.078 |
| 518 | 0.073 |
| 520 | 0.068 |
| 522 | 0.064 |
| 524 | 0.059 |
| 526 | 0.054 |
| 528 | 0.050 |
| 530 | 0.045 |
| 532 | 0.040 |
| 534 | 0.037 |
| 536 | 0.033 |
| 538 | 0.031 |
| 540 | 0.028 |
| 542 | 0.025 |
| 544 | 0.023 |
| 546 | 0.021 |
| 548 | 0.020 |
| 550 | 0.018 |
| 552 | 0.017 |
| 554 | 0.016 |
| 556 | 0.015 |
| 558 | 0.013 |
| 560 | 0.012 |
| 562 | 0.012 |
| 564 | 0.011 |
| 566 | 0.010 |
| 568 | 0.009 |
| 570 | 0.009 |
| 572 | 0.008 |
| 574 | 0.007 |
| 576 | 0.006 |
| 578 | 0.006 |
| 580 | 0.005 |
| 582 | 0.005 |

TABLE 3-continued

| λ (nm) | I (a.u.) |
|---|---|
| 584 | 0.005 |
| 586 | 0.004 |
| 588 | 0.004 |
| 590 | 0.004 |
| 592 | 0.004 |
| 594 | 0.003 |
| 596 | 0.003 |
| 598 | 0.003 |
| 600 | 0.003 |

Table 4 below shows the intensity difference ΔI between normalized left-handed emission and normalized right-handed emission values between 250 nm and 600 nm of P-H6$(CN)_2$ (solid line) and M-H6$(CN)_2$ (dotted line) and corresponds to FIG. 3 (in the table "yEx" stands for "y×$10^x$"). It can be seen that the difference between normalized left-handed emission and normalized right-handed emission for the P and M configurations of H6$(CN)_2$ are mostly symmetrical through a line of coordinate 0. Further, since the normalization is based on the highest peak of the total emission spectrum normalized at a value of 2 (unlike in FIG. 2), the value of ΔI at the wavelength of the highest total intensity peak gives the $g_{lum}$. The $g_{lum}$ value of H6$(CN)_2$ was found to be about $3\times10^{-2}$. It has, however, no TADF property.

TABLE 4

| | ΔI (a.u.) | |
|---|---|---|
| λ (nm) | P-H6$(CN)_2$ | M-H6$(CN)_2$ |
| 380 | −2.27E−04 | — |
| 385 | −2.23E−04 | −5.90E−04 |
| 390 | −1.93E−04 | −5.82E−04 |
| 395 | −1.37E−04 | −6.20E−04 |
| 400 | −9.41E−05 | −8.07E−04 |
| 405 | 2.23E−04 | −9.93E−04 |
| 410 | 1.41E−03 | −2.39E−03 |
| 415 | 5.72E−03 | −6.58E−03 |
| 420 | 1.44E−02 | −1.47E−02 |
| 425 | 2.29E−02 | −2.36E−02 |
| 430 | 2.74E−02 | −2.77E−02 |
| 435 | 2.41E−02 | −2.40E−02 |
| 440 | 1.85E−02 | −1.92E−02 |
| 445 | 1.56E−02 | −1.56E−02 |
| 450 | 1.62E−02 | −1.69E−02 |
| 455 | 1.69E−02 | −1.82E−02 |
| 460 | 1.56E−02 | −1.68E−02 |
| 465 | 1.32E−02 | −1.30E−02 |
| 470 | 9.60E−03 | −1.02E−02 |
| 475 | 7.36E−03 | −8.28E−03 |
| 480 | 6.33E−03 | −6.73E−03 |
| 485 | 5.25E−03 | −5.95E−03 |
| 490 | 4.34E−03 | −4.96E−03 |
| 495 | 3.55E−03 | −3.65E−03 |
| 500 | 2.57E−03 | −2.96E−03 |
| 505 | 1.67E−03 | −2.35E−03 |
| 510 | 1.40E−03 | −1.99E−03 |
| 515 | 8.96E−04 | −1.69E−03 |
| 520 | 7.12E−04 | −1.65E−03 |
| 525 | 5.63E−04 | −1.08E−03 |
| 530 | 2.85E−04 | −1.26E−03 |
| 535 | 2.34E−04 | −8.30E−04 |
| 540 | 1.16E−04 | −8.40E−04 |
| 545 | 7.35E−05 | −8.60E−04 |
| 550 | −6.46E−05 | −8.11E−04 |
| 555 | −8.35E−05 | −7.51E−04 |
| 560 | −1.22E−04 | −6.27E−04 |
| 565 | −1.73E−04 | −7.16E−04 |
| 570 | −1.59E−04 | −6.41E−04 |
| 575 | −1.49E−04 | −5.58E−04 |

TABLE 4-continued

| | ΔI (a.u.) | |
|---|---|---|
| λ (nm) | P-$H6(CN)_2$ | M-$H6(CN)_2$ |
| 580 | −2.15E−04 | −6.59E−04 |
| 585 | −1.74E−04 | −5.70E−04 |
| 590 | −2.01E−04 | −5.80E−04 |
| 595 | −2.19E−04 | −5.89E−04 |
| 600 | −1.96E−04 | −5.59E−04 |

In order to test the combination consisting of dt-BuCbzSulfone doped with $H6(CN)_2$, five doping ratios (1, 5, 10 and 20 mol. % of the total amount of dt-BuCbzSulfone) were made and spin-coated onto a substrate into a solid film. Luminescence measurements are provided in FIG. 4 from 370 nm to 650 nm, with values further shown in Table 5 below (in the table "yEx" stands for "$y\times10^x$"; "CP" stands for "$H6(CN)_2$ alone", "TADF" for "dt-BuCbzSulfone alone" and "x %" for "dt-BuCbzSulfone doped with x mol. % of $H6(CN)_2$").

TABLE 5

| λ (nm) | CP | TADF | 1% | 5% | 10% | 20% |
|---|---|---|---|---|---|---|
| 370 | 2.07E+05 | 7.44E+05 | 4.98E+05 | 5.41E+05 | 3.55E+05 | 6.20E+05 |
| 375 | 1.02E+05 | 1.13E+06 | 3.26E+05 | 3.01E+05 | 2.27E+05 | 2.97E+05 |
| 380 | 7.21E+04 | 2.43E+06 | 3.77E+05 | 2.97E+05 | 2.00E+05 | 1.73E+05 |
| 385 | 5.11E+04 | 4.92E+06 | 5.14E+05 | 3.84E+05 | 1.97E+05 | 1.33E+05 |
| 390 | 4.45E+04 | 8.99E+06 | 7.63E+05 | 5.36E+05 | 2.33E+05 | 1.15E+05 |
| 395 | 3.83E+04 | 1.47E+07 | 1.07E+06 | 6.65E+05 | 2.51E+05 | 1.21E+05 |
| 400 | 3.88E+04 | 2.09E+07 | 1.36E+06 | 8.70E+05 | 2.72E+05 | 1.43E+05 |
| 405 | 3.70E+04 | 2.66E+07 | 1.70E+06 | 1.10E+06 | 2.88E+05 | 2.02E+05 |
| 410 | 3.71E+04 | 2.99E+07 | 2.04E+06 | 1.36E+06 | 2.98E+05 | 2.81E+05 |
| 415 | 5.50E+04 | 3.12E+07 | 2.75E+06 | 1.97E+06 | 4.08E+05 | 5.82E+05 |
| 420 | 1.15E+05 | 3.12E+07 | 5.73E+06 | 4.80E+06 | 8.06E+05 | 1.96E+06 |
| 425 | 2.34E+05 | 3.00E+07 | 1.27E+07 | 1.18E+07 | 1.98E+06 | 6.06E+06 |
| 430 | 3.59E+05 | 2.84E+07 | 1.51E+07 | 1.46E+07 | 2.73E+06 | 9.18E+06 |
| 435 | 4.33E+05 | 2.63E+07 | 1.25E+07 | 1.23E+07 | 2.36E+06 | 8.70E+06 |
| 440 | 3.84E+05 | 2.39E+07 | 9.25E+06 | 9.10E+06 | 1.72E+06 | 6.97E+06 |
| 445 | 3.13E+05 | 2.13E+07 | 7.82E+06 | 7.64E+06 | 1.35E+06 | 5.60E+06 |
| 450 | 2.91E+05 | 1.88E+07 | 8.89E+06 | 8.75E+06 | 1.50E+06 | 5.97E+06 |
| 455 | 3.10E+05 | 1.65E+07 | 1.01E+07 | 1.01E+07 | 1.74E+06 | 7.14E+06 |
| 460 | 3.42E+05 | 1.41E+07 | 9.11E+06 | 9.24E+06 | 1.63E+06 | 7.18E+06 |
| 465 | 3.31E+05 | 1.21E+07 | 6.97E+06 | 7.18E+06 | 1.25E+06 | 5.89E+06 |
| 470 | 3.07E+05 | 1.04E+07 | 5.41E+06 | 5.51E+06 | 9.81E+05 | 4.61E+06 |
| 475 | 2.80E+05 | 8.93E+06 | 4.49E+06 | 4.56E+06 | 7.81E+05 | 3.76E+06 |
| 480 | 2.39E+05 | 7.64E+06 | 4.07E+06 | 4.00E+06 | 6.89E+05 | 3.31E+06 |
| 485 | 2.30E+05 | 6.46E+06 | 3.77E+06 | 3.74E+06 | 6.54E+05 | 3.03E+06 |
| 490 | 2.14E+05 | 5.61E+06 | 3.24E+06 | 3.31E+06 | 5.86E+05 | 2.72E+06 |
| 495 | 1.92E+05 | 4.66E+06 | 2.68E+06 | 2.70E+06 | 4.85E+05 | 2.30E+06 |
| 500 | 1.77E+05 | 3.99E+06 | 2.11E+06 | 2.16E+06 | 4.16E+05 | 1.88E+06 |
| 505 | 1.75E+05 | 3.38E+06 | 1.70E+06 | 1.74E+06 | 3.23E+05 | 1.53E+06 |
| 510 | 1.58E+05 | 2.92E+06 | 1.40E+06 | 1.42E+06 | 2.81E+05 | 1.25E+06 |
| 515 | 1.47E+05 | 2.44E+06 | 1.19E+06 | 1.19E+06 | 2.38E+05 | 1.04E+06 |
| 520 | 1.36E+05 | 2.11E+06 | 9.93E+05 | 9.87E+05 | 2.10E+05 | 8.98E+05 |
| 525 | 1.22E+05 | 1.76E+06 | 8.67E+05 | 8.71E+05 | 1.82E+05 | 7.53E+05 |
| 530 | 1.08E+05 | 1.54E+06 | 7.17E+05 | 7.17E+05 | 1.48E+05 | 6.53E+05 |
| 535 | 9.97E+04 | 1.36E+06 | 6.40E+05 | 6.29E+05 | 1.41E+05 | 5.54E+05 |
| 540 | 9.67E+04 | 1.19E+06 | 5.06E+05 | 5.07E+05 | 1.19E+05 | 4.57E+05 |
| 545 | 9.13E+04 | 1.00E+06 | 4.48E+05 | 4.22E+05 | 1.03E+05 | 3.99E+05 |
| 550 | 8.34E+04 | 9.05E+05 | 3.71E+05 | 3.76E+05 | 7.38E+04 | 3.58E+05 |
| 555 | 7.60E+04 | 7.68E+05 | 3.33E+05 | 3.14E+05 | 7.96E+04 | 3.02E+05 |
| 560 | 7.38E+04 | 6.80E+05 | 2.61E+05 | 2.87E+05 | 8.17E+04 | 2.59E+05 |
| 565 | 6.10E+04 | 6.00E+05 | 2.56E+05 | 2.46E+05 | 6.65E+04 | 2.27E+05 |
| 570 | 6.02E+04 | 5.28E+05 | 2.01E+05 | 1.99E+05 | 5.40E+04 | 1.93E+05 |
| 575 | 6.05E+04 | 4.57E+05 | 1.84E+05 | 1.76E+05 | 6.63E+04 | 1.75E+05 |
| 580 | 5.53E+04 | 4.03E+05 | 1.77E+05 | 1.69E+05 | 5.30E+04 | 1.69E+05 |
| 585 | 5.16E+04 | 3.47E+05 | 1.47E+05 | 1.27E+05 | 4.78E+04 | 1.46E+05 |
| 590 | 5.15E+04 | 3.03E+05 | 1.29E+05 | 1.23E+05 | 5.30E+04 | 1.30E+05 |
| 595 | 4.80E+04 | 3.01E+05 | 1.01E+05 | 1.10E+05 | 4.26E+04 | 1.19E+05 |
| 600 | 5.19E+04 | 2.50E+05 | 1.06E+05 | 9.26E+04 | 4.93E+04 | 1.13E+05 |
| 605 | 4.56E+04 | 2.30E+05 | 9.89E+04 | 9.77E+04 | 3.83E+04 | 1.04E+05 |
| 610 | 4.92E+04 | 2.12E+05 | 1.07E+05 | 9.95E+04 | 4.38E+04 | 1.01E+05 |
| 615 | 4.30E+04 | 2.19E+05 | 9.00E+04 | 8.39E+04 | 4.17E+04 | 9.02E+04 |
| 620 | 4.60E+04 | 1.77E+05 | 9.22E+04 | 9.38E+04 | 4.35E+04 | 8.87E+04 |
| 625 | 4.96E+04 | 1.57E+05 | 8.06E+04 | 7.88E+04 | 4.10E+04 | 8.53E+04 |
| 630 | 4.40E+04 | 1.56E+05 | 7.82E+04 | 9.24E+04 | 6.06E+04 | 8.60E+04 |
| 635 | 5.96E+04 | 1.42E+05 | 7.17E+04 | 7.53E+04 | 4.18E+04 | 8.82E+04 |
| 640 | 7.43E+04 | 1.68E+05 | 7.53E+04 | 8.48E+04 | 6.31E+04 | 1.07E+05 |
| 645 | 5.70E+04 | 1.68E+05 | 8.56E+04 | 8.31E+04 | 4.79E+04 | 1.07E+05 |
| 650 | 7.65E+04 | 1.39E+05 | 9.07E+04 | 9.07E+04 | 5.42E+04 | 1.11E+05 |

Table 6 below shows the intensity difference ΔI between normalized left-handed emission and normalized right-handed emission values between approximately 400 nm and 650 nm of dt-BuCbzSulfone alone (TADF) and compositions constituting of dt-BuCbzSulfone with P-H6$(CN)_2$ (P-CP; dotted line) and M-H6$(CN)_2$ (M-CP; solid line) at 10 mol. % of the total amount of dt-BuCbzSulfone (in the table "yEx" stands for "$y\times10^{x}$"). Table 6 corresponds to FIG. 5. It can be seen that the difference between normalized left-handed emission and normalized right-handed emission for the P and M configurations of H6$(CN)_2$ are mostly symmetrical through a line of coordinate 0. Further, since the normalization is based on the highest peak of the total emission spectrum normalized at a value of 2, the value of ΔI at the wavelength of the highest total emission peak gives the $g_{lum}$. From Table 5, it can be seen that the maximum intensity for dt-BuCbzSulfone with 10 mol. % H6$(CN)_2$ corresponds to a wavelength of 430 nm. From Table 6, it can be seen that at 430 nm, the values of ΔI (thus the value of $g_{lum}$) are $1.59\times10^{-2}$ and $1.44\times10^{-2}$ for the composition with M-H6$(CN)_2$ and P-H6$(CN)_2$, respectively.

TABLE 6

| λ (nm) | TADF | M-CP | P-CP |
|---|---|---|---|
| 380 | 7.19E−03 | 1.70E−03 | 2.77E−03 |
| 385 | 4.83E−03 | 8.68E−04 | 2.00E−03 |
| 390 | 3.96E−03 | −6.87E−05 | 1.42E−03 |
| 395 | 3.10E−03 | −9.80E−04 | 8.39E−04 |
| 400 | 2.33E−03 | −7.21E−04 | 8.30E−04 |
| 405 | 1.55E−03 | 2.29E−05 | 1.21E−03 |
| 410 | 1.07E−03 | 1.93E−05 | 1.55E−03 |
| 415 | 6.44E−04 | −1.47E−03 | 2.64E−03 |
| 420 | 1.21E−04 | −6.03E−03 | 5.97E−03 |
| 425 | 3.16E−04 | −1.14E−02 | 1.07E−02 |
| 430 | 4.81E−04 | −1.59E−02 | 1.44E−02 |
| 435 | 2.83E−04 | −1.61E−02 | 1.56E−02 |
| 440 | 5.28E−04 | −1.37E−02 | 1.33E−02 |
| 445 | 3.48E−04 | −1.14E−02 | 1.13E−02 |
| 450 | −2.57E−05 | −1.09E−02 | 1.03E−02 |
| 455 | −3.14E−04 | −1.13E−02 | 1.07E−02 |
| 460 | −2.30E−04 | −1.14E−02 | 1.06E−02 |
| 465 | −1.32E−04 | −1.01E−02 | 9.55E−03 |
| 470 | −8.78E−05 | −8.29E−03 | 7.54E−03 |
| 475 | 3.71E−04 | −6.53E−03 | 6.01E−03 |
| 480 | 1.81E−04 | −5.13E−03 | 5.03E−03 |
| 485 | 2.74E−05 | −4.63E−03 | 4.01E−03 |
| 490 | 2.70E−04 | −3.92E−03 | 3.71E−03 |
| 495 | 2.55E−04 | −3.39E−03 | 2.92E−03 |
| 500 | 2.94E−04 | −2.81E−03 | 2.45E−03 |
| 505 | 5.47E−04 | −2.26E−03 | 1.85E−03 |
| 510 | 4.70E−04 | −1.62E−03 | 1.33E−03 |
| 515 | 3.59E−04 | −1.48E−03 | 1.25E−03 |
| 520 | 4.40E−04 | −1.21E−03 | 1.11E−03 |
| 525 | 4.90E−04 | −9.76E−04 | 7.24E−04 |
| 530 | 3.94E−04 | −7.41E−04 | 8.32E−04 |
| 535 | 4.83E−04 | −6.93E−04 | 6.93E−04 |
| 540 | 4.65E−04 | −5.88E−04 | 5.58E−04 |
| 545 | 4.25E−04 | −4.67E−04 | 5.51E−04 |
| 550 | 4.93E−04 | −4.37E−04 | 4.12E−04 |
| 555 | 4.70E−04 | −3.45E−04 | 4.36E−04 |
| 560 | 4.60E−04 | −9.08E−05 | 3.19E−04 |
| 565 | 4.42E−04 | −1.89E−04 | 3.48E−04 |
| 570 | 4.30E−04 | −7.53E−05 | 3.59E−04 |
| 575 | 3.92E−04 | −1.39E−04 | 2.12E−04 |
| 580 | 3.50E−04 | −7.02E−05 | 2.94E−04 |
| 585 | 4.05E−04 | −2.22E−05 | 2.43E−04 |
| 590 | 3.75E−04 | −2.97E−05 | 2.99E−04 |
| 595 | 4.16E−04 | −5.76E−05 | 2.20E−04 |
| 600 | 3.36E−04 | 3.00E−05 | 1.59E−04 |
| 605 | 3.44E−04 | −1.60E−06 | 1.35E−04 |
| 610 | 3.20E−04 | −7.47E−05 | 9.78E−05 |
| 615 | 3.84E−04 | −6.42E−06 | 1.81E−04 |
| 620 | 3.72E−04 | 6.25E−05 | 2.25E−04 |
| 625 | 3.69E−04 | 1.02E−04 | 1.90E−04 |
| 630 | 3.18E−04 | 2.50E−04 | 2.96E−04 |
| 635 | 3.53E−04 | 9.92E−05 | 2.75E−04 |
| 640 | 3.02E−04 | 1.02E−04 | 2.03E−04 |
| 645 | 2.67E−04 | 1.29E−04 | 1.87E−04 |
| 650 | 2.60E−04 | 1.50E−04 | 1.96E−04 |

Dt-BuCbzSulfone has singlet and triplet states at a higher energy level than the singlet of H6$(CN)_2$ which is at 2.99 eV at 415 nm and 2.92 eV at 425 nm. Moreover, the luminescence spectrum of dt-BuCbzSulfone overlaps the absorption spectrum of H6$(CN)_2$.

These results show that even at only 1% of dopant, luminescence transfer from the TADF molecule to the CP molecule is quantitative, which provide evidence of transfer of unpolarized luminescence from the TADF molecule to the CP molecule providing circularly polarized luminescence. The intensity of the overall luminescence decreases as the ratio of H6$(CN)_2$ in dt-BuCbzSulfone decreases from 1 mol. % to 10 mol. %. However, from 10 mol. % to 20 mol. % it increases instead. The composition of example 1 provides a cyan blue colour.

Example 8

The CP molecule of Example 7 can be replaced by H6$(NPh)_2$ or H6$(DPP)_2$.

Figure 6:
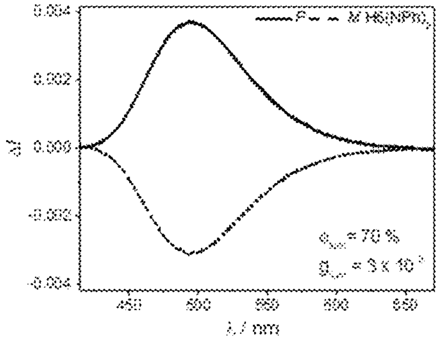
FIG. 6 is a graph showing the intensity difference ΔI between left-handed emitted light and right-handed emitted light of M-$H6(NPh)_2$ (dotted line) and P-$H6(NPh)_2$ (solid line) approximately between 400 nm and 650 nm recorded in dichloromethane solvent at room temperature. The values are normalized so that the highest peak value $I_{max}$ of the total emission ($I_R$+$I_L$) is normalized to 2. In such situation, the value of ΔI at the wavelength of $I_{max}$ is the $g_{lum}$ value at that wavelength.

FIG. 6 shows the intensity difference ΔI between left-handed luminescence light and right-handed luminescence light of P-H6$(NPh)_2$ (solid line) and M-H6$(NPh)_2$ (dotted line) are shown. It can be observed that P-H6$(NPh)_2$ emits more left-handed light than right-handed light so that it can be said that P-H6-$(NPh)_2$ emits a left-handed circular polarized light to some extent. Similarly, M-H6$(NPh)_2$ emits more right-handed light than left-handed light so that it can be said that M-H6-$(NPh)_2$ emits a right-handed circular polarized light to some extent. The maximum value of ΔI for both molecules was observed close to 495 nm. H6$(NPh)_2$ has a luminescence quantum yield of 70% and a luminescence dissymmetry factor of $3\times10^{-3}$. H6$(NPh)_2$ provides a green colour.

Figure 7:
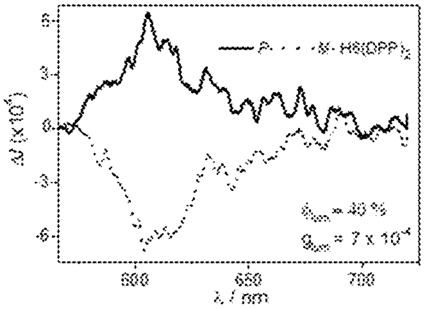
FIG. 7 is a graph showing the intensity difference ΔI between left-handed emitted light and right-handed emitted light of M-$H6(DPP)_2$ (dotted line) and P-$H6(DPP)_2$ (solid line) approximately between 550 nm and 725 nm recorded in dichloromethane solvent at room temperature. The values are normalized so that the highest peak value $I_{max}$ of the total emission ($I_R$+$I_L$) is normalized to 2. In such situation, the value of ΔI at the wavelength of $I_{max}$ is the $g_{lum}$ value at that wavelength.

FIG. 7 shows the intensity difference ΔI between left-handed luminescence light and right-handed luminescence light of P-H6$(DPP)_2$ (solid line) and M-H6$(DPP)_2$ (dotted line). It can be observed that P-H6$(DPP)_2$ emits more left-handed light than right-handed light so that it can be said that P-H6-$(DPP)_2$ emits a left-handed circular polarized light to some extent. Similarly, M-H6$(DPP)_2$ emits more right-handed light than left-handed light so that it can be said that M-H6-$(DPP)_2$ emits a right-handed circular polarized light to some extent. The maximum value of ΔI for both molecules was observed close to 605 nm. H6$(DPP)_2$ has a luminescence quantum yield of 40% and a luminescence dissymmetry factor of $7\times10^{-4}$. H6$(DPP)_2$ provides a red colour.

The TADF molecule of Example 7 can be replaced by Cbz-TRZ2 or 4-CbzIPN which are described in Adachi et al., 2017 [4] and Adachi et al., 2012 [5] respectively. Cbz-TRZ2 has a TADF quantum yield of 86%, whereas it is 94% for 4-CbzIPN.

The following combinations provide particularly good results: Cbz-TRZ2 with H6$(NPh)_2$ and 4-CbzIPN with H6$(DPP)_2$.

In addition to the TADF molecules and CP molecules described herein, many possible associations of TADF molecules and CP molecules can be contemplated in order to obtain the desired synergetic CP-TADF property. For instance, one can think about other helicene derivatives, helicenoid compounds (where the helical polycyclic compound is not fully conjugated), biarylic systems, and chiral molecules with planar chirality such as paracyclophane derivatives for the CP molecule.

BIBLIOGRAPHY

[1] Longhi, G.; Castiglioni, E.; Koshoubu, J.; Mazzeo, G.; Abbate, S., "Circularly Polarized Luminescence: A Review of Experimental and Theoretical Aspects", *Chirality* 2016, 28 (10), 696-707

[2] Dhbaibi, K.; Favereau, L.; Srebro-Hooper, M.; Jean, M.; Vanthuyne, N.; Zinna, F.; Jamoussi, B.; Di Bari, L.; Autschbach, J.; Cras sous, J., "Exciton coupling in diketopyrrolopyrrole-helicene derivatives leads to red and near-infrared circularly polarized luminescence", *Chem. Sci.* 2018, 9, 735-742

[3] Zhang, Q.; Li, J.; Shizu, K.; Huang, S.; Hirata, S.; Miyazaki, H.; Adachi, C., "Design of Efficient Thermally Activated Delayed Fluorescence Materials for Pure Blue Organic Light Emitting Diodes", *J. Am. Chem. Soc.,* 134, 36, 14706-14709 (2012)

[4] Cui, L.-S.; Nomura, H.; Geng, Y.; Kim, J. U.; Nakanotani, H.; Adachi, C., "Controlling Singlet-Triplet Energy Splitting for Deep-Blue Thermally Activated Delayed Fluorescence Emitters", *Angew. Chem. Int. Ed.,* 56, 1571 (2017)

[5] Uoyama, H.; Goushi, K.; Shizu, K.; Nomura, H.; Adachi, C., "Highly efficient organic light-emitting diodes from delayed fluorescence", *Nature,* 492, 234-238 (2012).

The invention claimed is:

1. An active light-emitting layer composition comprising a TADF molecule with TADF properties as a host material and a luminescent molecule with circular polarisation properties as a dopant;

wherein the luminescent molecule is carbo[6]helicene derivate with the general formula, in an M or P configuration:

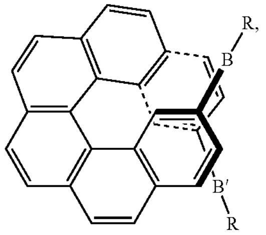

wherein B' is a linker and R is a chemical group.

2. The active light-emitting layer composition of claim 1, wherein the TADF molecule exhibits a singlet state energy level and a triplet state energy level and the luminescent molecule exhibits a singlet state energy level lower than the singlet state and triplet state energy levels of the TADF molecule.

3. The active light-emitting layer composition of claim 1, wherein the luminescent molecule has an absorption spectrum and the TADF molecule has a luminescence spectrum overlapping the absorption spectrum of the luminescent molecule.

4. The active light-emitting layer composition of claim 1, wherein the composition exhibits at least one of the following properties:

a TADF quantum yield of 0.01 or higher;

a luminescence quantum yield of 0.10 or higher; and a luminescence polarization measured through the $g_{lum}$ value which is different from 0.

5. The active light-emitting layer composition of claim 1, wherein the luminescent molecule is a chiral molecule selected from the group consisting of a helicene derivative, a helicenoid compound, a biarylic system, and a molecule with planar chirality.

6. The active light-emitting layer composition of claim 1, wherein B' is a linker with one of the following formulae:

A: ----≡----;

(ethyne-1,2-diyl)

B: 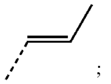 ;

(E-ethene-1,2-diyl)

C: 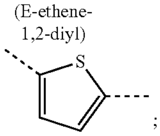 ;

(tiophene-2,5-diyl)

D: 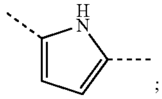 ;

(pyrole-2,5-diyl)

E: 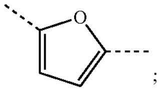 ;

(furane-2,5-diyl)

F: 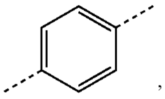 , (benzene-1,4-diyl)

or a combination thereof.

7. The active light-emitting layer composition of claim 1, wherein R is one of the following formulae:

G: 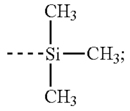

(trimethylsilyle)

H: 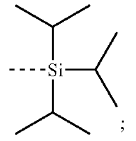 ;

(triisopropylsilyle)

I: ----C≡N;

(cyanyle)

J: ----$NH_2$;

(aminyle)

-continued

K: 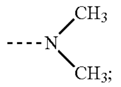

(dimethylaminyle)

L: 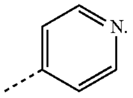

(4-pyridinyle)

8. The active light-emitting layer composition of claim 1, wherein the luminescent molecule is one of:

4,4'-(hexahelicene-2,15-diylbis(ethyne-2,1-diyl))dibenzonitrile;

4,4'-(hexahelicene-2,15-diylbis(ethyne-2,1-diyl))dipyridine;

4,4'-(hexahelicene-2,15-diylbis(ethyne-2,1-diyl))dianiline;

4,4'-(hexahelicene-2,15-diylbis(ethyne-2,1-diyl))di(N,N-dimethylaniline);

4,4'-(hexahelicene-2,15-diylbis(ethyne-2,1-diyl))di(trimethylsilane);

4,4'-(hexahelicene-2,15-diylbis(ethyne-2,1-diyl))di(N-hexyl-1,8-naphthalimide); and 4,4'-(hexahelicene-2,15-diylbis(ethyne-2,1-diyl))di(2,5-N-octyl-3,6-di-2-thienyl-pyrrolo[3,4-c] pyrrole-1,4-dione);

in their P or M isomeric configuration.

9. The active light-emitting layer composition of claim 1, wherein the TADF molecule is an achiral molecule.

10. The active light-emitting layer composition of claim 1, with one of the following combination of TADF molecule and luminescent molecule:

9,9'-(sulfonylbis(4,1-phenylene))bis(3,6-di-tert-butyl-9H-carbazole) and 4,4'-(hexahelicene-2,15-diylbis(ethyne-2,1-diyl))dibenzonitrile;

9-(4-(4,6-diphenyl-1,3,5-triazin-2-yl)phenyl)-1,3,6,8-tetramethyl-9H-carbazole and 4,4'-(hexahelicene-2,15-diylbis(ethyne-2,1-diyl))di(N-hexyl-1,8-naphthalimide; and 2,4,5,6-tetra(9H-carbazol-9-yl)isophthalonitrile and 4,4'-(hexahelicene-2,15-diylbis(ethyne-2,1-diyl))di(2,5-N-octyl-3,6-di-2-thienyl-pyrrolo [3,4-c] pyrrole-1,4-dione).

11. A light-emitting device having an active light-emitting layer made of the active light-emitting layer composition of claim 1.

12. The light-emitting device of claim 11, wherein the light-emitting device is an OLED.

13. An active light emitting layer composition comprising a TADF molecule with TADF properties as a host material and a luminescent molecule with circular polarisation properties as a dopant;

wherein the achiral molecule is one of the following:

9,9'-(sulfonylbis(4,1-phenylene))bis(3,6-di-tert-butyl-9H-carbazole);

9-(4-(4,6-diphenyl-1,3,5-triazin-2-yl)phenyl)-1,3,6,8-tetramethyl-9H-carbazole; and 2,4,5,6-tetra(9H-carbazol-9-yl)isophthalonitrile.

* * * * *